United States Patent [19]

Kelman

[11] 4,296,501

[45] Oct. 27, 1981

[54] INTRAOCULAR LENS AND METHOD OF MAKING THE SAME

[76] Inventor: Charles D. Kelman, 269 Grand Central Pkwy., Floral Park, N.Y. 11005

[21] Appl. No.: 168,544

[22] Filed: Jul. 14, 1980

[51] Int. Cl.³ .......................... A61F 1/16; A61F 1/24
[52] U.S. Cl. ......................................................... 3/13
[58] Field of Search .......................................... 3/13, 1

[56] References Cited

U.S. PATENT DOCUMENTS

| | | | |
|---|---|---|---|
| 4,092,743 | 6/1978 | Kelman | 3/13 |
| 4,134,160 | 1/1979 | Bayers | 3/13 |
| 4,134,161 | 1/1979 | Bayers | 3/13 |
| 4,159,546 | 7/1979 | Shearing | 3/13 |

Primary Examiner—Ronald L. Frinks
Attorney, Agent, or Firm—Henry Sternberg

[57] ABSTRACT

An intraocular lens for use as an artificial lens implant anteriorly of the iris which has a pair of position fixation elements providing a three-point support for the lens. One of the position fixation elements has a portion swivelable about a base portion attached to the lens body so that the position fixation element may be adjusted to provide a three-point support corresponding to measured dimensions of the eye and may be attached in the selected position by sutures before implantation in the eye.

14 Claims, 8 Drawing Figures

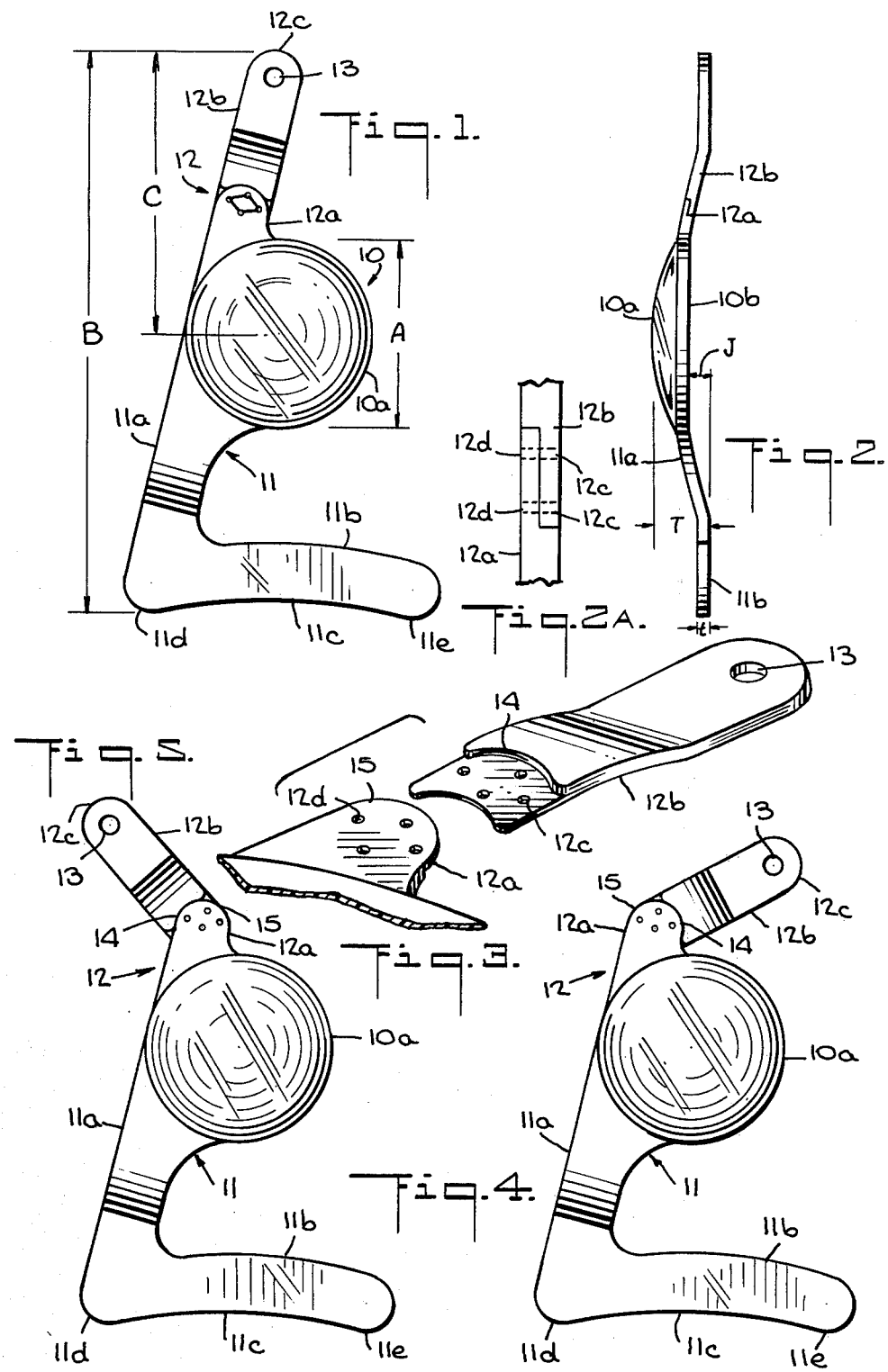

INTRAOCULAR LENS AND METHOD OF MAKING THE SAME

This invention relates to intraocular lenses of the type suitable for use as an artificial lens implant anteriorly of the iris. A lens of this type is described and claimed in my U.S. Pat. No. 4,092,743 entitled "Intraocular Lenses".

As is well known to those skilled in this art, even though the diameter of the lens body of an intraocular lens is only about 4 millimeters, for the purpose of a lens implantation, a corneo-scleral incision considerably longer than the lens body diameter, and normally from about 8 to 9 millimeters in length is ordinarily required for lenses other than the type described and claimed in U.S. Pat. No. 4,092,473. An incision of this magnitude is mandated because the incision must be capable of being spread far enough to accomodate both the thickness and the width of the lens. In this context, "thickness" means the dimension of the lens as measured from the anteriormost plane in which any part of the lens structure (e.g., the apex of the lens body) is found, to the posteriormost plane (e.g., the plane of the position fixation elements). "Width" means the minimum length of the projection of a lens onto a plane parallel to the optical axis of the lens body, in a direction perpendicular to a projection of the optical axis on such plane which can be achieved by rotating the lens 360° about said optical axis.

In a lens of the type described and claimed in U.S. Pat. No. 4,092,743, an intraocular lens construction is characterized by a medial lens body and only two position fixation elements projecting from spaced, generally opposite lateral regions of the lens body. One of these elements has a first portion extending generally laterally from the lens body and a second portion extending from the end of the first portion generally transversely thereto and at least partly peripherally of the lens body, while the other element extends generally laterally from the lens body. The maximum width of any portion of either position fixation element for a given thickness thereof is such that it can be accomodated in and passed through the minimum length incision which is required to accomodate and permit passage of the lens body. Preferably, both elements are unitary with the lens body, i.e. they are not separately attached elements but are formed with the lens body (by molding or machining, for example) of a single block of any suitable physiologically inert and non-toxic synthetic plastic material such as are well-known to the art, e.g. polymethylmethacrylate, but the position fixation elements may, as long as they have the requisite shapes and orientations, be constituted by platinum-iridium or equivalent metal wire loops with each wire loop being anchored at its two ends on the anterior or posterior surface of the lens body.

In a lens of the type described and claimed in U.S. Pat. No. 4,092,743, the first portion or leg of the first position fixation element which is contiguous to the lens body extends generally laterally of the lens body, while the transverse second portion of the element extends from the leg or first portion at least partly peripherally of the lens body. The second portion must, however, be at a spacing from the periphery of the lens body sufficient easily to accomodate the thickness of the cornea and the sclera of the eye, and preferably its length will be sufficient for it to extend through an arc of between about 40° and about 60° along the periphery of the lens body, with the opposite end extremities of the second portion of the first position fixation element as used peripherally of the lens body being, respectively, located on two imaginary lines which are tangent to the lens body at opposite sides thereof and intersect at a point spaced from the lens body on the side thereof where the second position fixation element is located.

The lens construction can also be stated in somewhat different words: first, the configurations of the two position fixation elements and their location with respect to the lens body are such that the minimum length of a projection of the entire lens onto a plane parallel to the optical axis of the lens body in a direction perpendicular to a projection of the optical axis on that plane which can be achieved by rotating the lens 360° about the optical axis, is greater than the minimum length of a projection of the lens body alone onto that plane in a direction perpendicular to a projection of the optical axis on the plane which can be achieved by rotating the lens body 360° about the optical axis; second, the difference between lengths is sufficient that an insertion of the lens, through an incision in the eye by a movement which is generally radial with respect to the optical axis would require the length of the incision to be greater than the minimum possible length of the incision which, as a function of the thickness and lateral dimensions of the lens body, would accommodate and permit passage of the lens body alone; and third, the maximum width of each position fixation element at any part thereof for a given thickness thereof is such that the element can be accommodated in and passed longitudinally through said minimum length incision.

In use, when a lens of the type described is being implanted, the surgeon will first make a corneo-scleral incision in the eye only slightly longer than the diameter of the lens body, i.e., the incision will be about 5 millimeters in length. In order to introduce the lens into the eye, the surgeon will then introduce the lens essentially "longitudinally" into the eye, i.e., he will in effect snake the lens in through the incision starting from the free end extremity of the tranverse second portion of the first position fixation element and ending with the tip of the second element, until the lens is properly positioned in the eye.

Prior to inserting the lens in the eye, the surgeon will make measurements of the groove located behind the scleral spur for selecting a lens from a plurality of lenses for implantation in which the first and second position fixation elements are to be seated in front of the iris in the lower and upper regions, respectively, of the groove located behind the scleral spur. In this lens construction, both the first portion or leg of the first position fixation element and an inner first section of the second position fixation element, while extending generally laterally from the lens body, also are inclined somewhat posteriorly of the lens body and the transverse second portion of the first fixation element and the outer or second section of the second position fixation element are generally coplanar with each other, in a plane parallel to the posterior surface plane of the lens body. Thus, the two position fixation elements are not entirely coplanar with each other. It is contemplated that the degree of the said inclination of the first portion of the first position fixation element and the first section of the second position fixation element should be such that the perpendicular distance from the common posterior plane of the second portion of the first position fixation element and the second section of the second position fixation element to the posterior surface plane of the lens body is between about 0.25 and 0.75 millimeters and preferably about 0.5 millimeters. Additionally, the second or transverse portion of the first position fixation element preferably will have a slight degree of concavity, with a radius of curvature of about 180 millimeters, in that edge thereof which faces away from the lens body, so that at the opposite ends of the second portion there will be defined respective downwardly directed lobes or tip portions which, upon implantation of the lens, (by means of a "snaking in" procedure) will coact with the tip end of the second section of the second position fixation element, when the same are all received in the groove behind the scleral spur, to effect an essentially three-point position fixation of the lens in the eye. The arrangement thus is such that a small gap will be maintained between the region of the anterior surface of the iris bounding the pupil and the posterior surfaces of the first portion and first section of the first and second position fixation elements, so as to avoid possible irritation of the iris in that region.

For a lens of the type described, it has heretofore been necessary for the surgeon to have available to him at the time of the implantation a great number of lenses so that he can select one which will fit the dimensions of the eye.

It is an object of the present invention, therefore, to provide a new and improved intraocular lens and method of making the same which avoids one or more of the disadvantages of prior such lenses and methods of implanting the same anteriorly of the iris.

It is another object of the invention to minimize the number of lenses which the surgeon must have available to him at the time of an artificial lens implantation anteriorly of the iris to select one which corresponds with the measured dimensions of the eye.

In accordance with the invention, an intraocular lens suitable for use as an artificial lens implant anteriorly of the iris, comprises a medial, light-focusing lens body and at least a pair of lateral position fixation elements connected with the lens body. At least one of the pair of position fixation elements has a first portion contiguous to and extending generally laterally outwardly from a first region of the periphery of the lens body. The other of the pair of position fixation elements has a first portion contiguous to and extending generally laterally outwardly from a second region of the periphery of the lens body spaced from and generally opposite the first region and in a direction generally opposite to that of the first portion of the aforesaid one position fixation element. The other of the pair of position fixation elements has a second portion pivotable about the end of the first portion of the other of the pair of position fixation elements before being attached to the first portion of the other of the pair of position fixation elements before implantation in the eye. The position fixation elements cooperate to effect proper positioning and immobilization of the lens with respect to the iris of an eye of a lens implant patient.

Also in accordance with the invention, the method of making an intraocular lens having a lens body and at least a pair of position fixation elements connected with the lens body, a second portion of a position fixation element being pivotable about the end of a first portion thereof, comprises measuring predetermined dimensions of the eye. The method also includes pivoting the second portion about the first portion of a position fixation element to correspond with the measured dimensions of the eye and attaching the second portion to the first portion of the position fixation element in the selected position.

For a better understanding of the present invention, together with other and further objects thereof, reference is made to the following description, taken in connection with the accompanying drawings, and its scope will be pointed out in the appended claims.

Referring now to the drawings:

FIG. 1 is a plan view of an intraocular lens in accordance with the invention;

FIG. 2 is a side elevational view of the lens shown in FIG. 1;

FIG. 2a is a fragmentary side elevational view to an enlarged scale of a position fixation element of the FIG. 1 lens;

FIG. 3 is an enlarged perspective view of a portion of the FIG. 1 lens;

FIG. 4 is a plan view of the FIG. 1 lens with a portion of a position fixation element adjusted to correspond with measured dimensions of the eye;

FIG. 5 is another plan view of the FIG. 1 lens with the portion of the position fixation element adjusted to another position to correspond with the measured dimensions of the eye;

Figure 6:
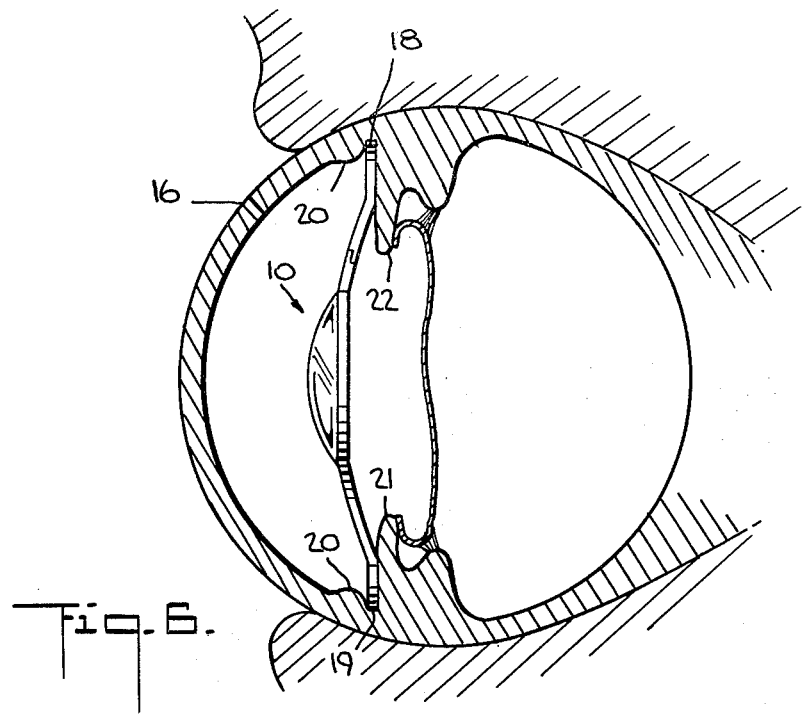
FIG. 6 is a diagrammatic vertical section through a human eye and shows a lens corresponding to the FIG. 4 lens implanted in the eye.

Referring now more particularly to FIG. 1 of the drawings, an intraocular lens suitable for use as an artificial lens implant anteriorly of the iris comprises a medial, light-focusing lens body 10a and at least a pair of lateral position fixation elements 11, 12 connected with the lens body 10a. At least one of the pair of position fixation elements 11 has a first portion 11a contiguous to and extending generally laterally outwardly from a first region of the periphery of the lens body 10.

The other of the pair of position fixation elements 12 has a first portion 12a contiguous to and extending generally outwardly from a second region of the periphery of the lens body 10a spaced from and generally opposite said first region and in a direction generally opposite to that of the first portion 11a of the one position fixation element 11.

The one of the position fixation elements 11 preferably has a second portion 11b extending from the first portion 11a generally transversely thereto and at least partially peripherally of the lens body 10a and spaced generally laterally outwardly from a third region of the periphery of the lens body. The position fixation elements 11, 12 cooperate to effect proper positioning and immobilization of the lens 10 with respect to the iris of an eye of a lens implant patient. The other of the pair of position fixation elements 12 has a second portion 12b pivotable about the end of the first portion of the position fixation element 12 before implantation in the eye.

Referring now to FIGS. 1 and 2 of the drawings, the other position fixation element 12 is preferably provided with means to facilitate manipulation of the lens during the insertion thereof into the eye comprising, for example, a medial aperture 13 provided in the other position fixation element 12. The position fixation elements 11, 12 are constructed and arranged such that the second portion 11b of the one position fixation element 11 and the tip end region 12c of the other position fixation element 12 coact to provide a three point support for properly positioning the lens in the eye. The second portion 11b of the one position fixation element 11 has a middle region 11c of that part of its peripheral edge which faces away from the lens body 10a disposed closer to the lens body 10a than the opposite end regions 11d, 11e of that edge. The ends 11d, 11e of the second portion 11b of the one position fixation element 11 and the tip end region 12c of the other position fixation element 12 provide the three point support.

The second portion 12b of the other of the pair of position fixation elements 11 and 12 is pivotable about the end of the first portion 12a of the other of the pair of position fixation elements 11, 12 before being attached to the end of the first portion of the other of the position fixation elements before implantation in the eye, as represented in FIGS. 4 and 5.

After the second portion 12b of the other of the pair of position fixation elements 11, 12 is attached to the end of the first portion 12a of the other of the pair of position fixation elements 11, 12, the configurations of the position fixation elements 11, 12 and their location with respect to the lens body 10a preferably are such that the minimum length of a projection of the entire lens onto a plane parallel to the optical axis of the lens body in a direction perpendicular to a projection of the optical axis on such plane which can be achieved by rotating the lens 360° about the optical axis is greater than the minimum length of a projection of the lens body onto the plane in a direction perpendicular to a projection of the optical axis on such plane which can be achieved by rotating the lens body 360° about the optical axis, to an extent sufficient that insertion of the lens into an incision in the eye, by a movement which is generally radial with respect to the optical axis would require the length of such incision to be greater than the minimum possible length of the incision which, as a function of the thickness and lateral dimensions of the lens body, would accommodate and permit passage therethrough of the lens body alone, and the maximum width of each of the position fixation elements at any part thereof for a given thickness thereof preferably is such that each element can be accommodated in and pass longitudinally through the minimum length incision in the eye, whereby the entire lens is capable of being snaked into the eye of the lens implantation through the minimum length incision.

The length of the second portion 11b of the one position fixation element 11 preferably is such that it extends along the periphery of the lens body through an arc of between about 40° and about 60°, preferably an arc of about 45°.

Figure 7:
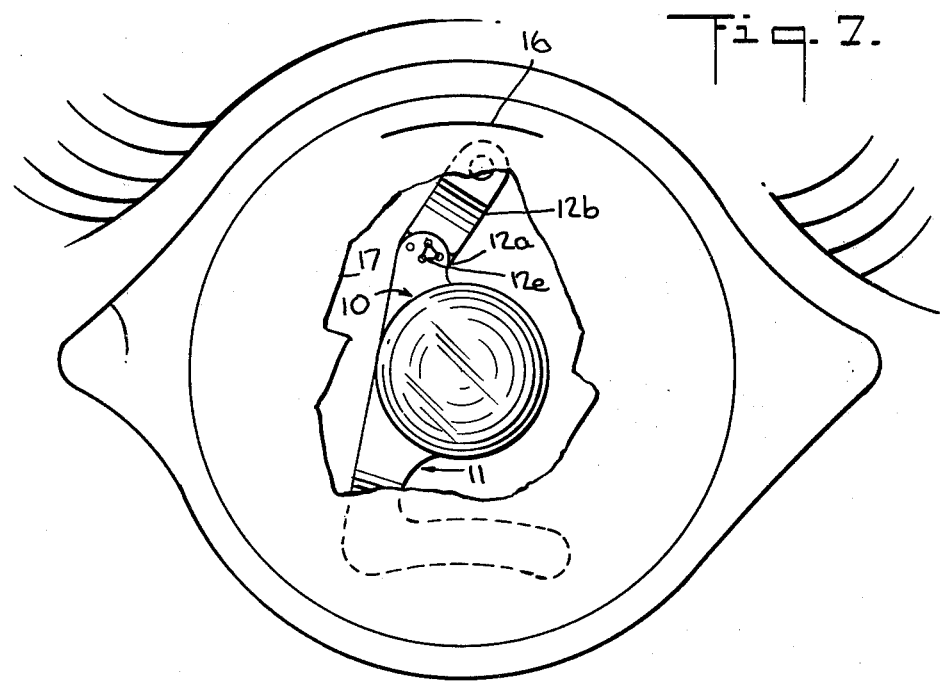
FIG. 7 is a front view of a human eye having the FIG. 6 lens implanted therein.

As represented in FIGS. 4 and 5, the second portion 12b of the other of the pair of position fixation elements is swivelable about the end of the first portion 12a of the other of the pair of position fixation elements 11, 12 before implantation in the eye. The second portion 12b of the other of the pair of position fixation elements has, for example, a concave surface 14 as represented in FIG. 3 and the end of the first portion 12a of the other of the pair of position fixation elements has, for example, a convex surface 15 mating with the concave surface 14. As represented in FIGS. 2a and 3, the portions 12a and 12b preferably overlap when attached and each portion has, for example, a plurality of apertures 12c and 12d, through selected ones of which sutures may be passed to attach the portions 12a and 12b together in selected relative angular positions. The position of the second portion 12b of the other of the pair of position fixation elements is adjusted about the end of the first portion 12a of the other of the pair of position fixation elements to a position represented, for example, in FIG. 7 before implantation in the eye through a corneal-scleral incision 16 as represented in FIGS. 6 and 7 to correspond with measured dimensions of the eye as represented in FIGS. 6 and 7. The second portion 12b of the other of the position fixation elements 12 preferably is attached by sutures 12e through the apertures 12c, 12d or may be, for example, welded by a laser beam to the first portion 12a at the desired position of adjustment before implantation in the eye if the material of the portions 12a, 12b is, even after welding, sufficiently inert that no toxic reaction in the eye will be caused in the future. For the sake of simplicity, in FIG. 7 a part of the cornea 17 is illustrated broken away, and the internal elements of the eye, such as the iris, the posterior capsules and the zonules have been omitted entirely. The incision preferably is made about 5 millimeters long, i.e. just sufficient to enable it to be spread to the degree required to accommodate both the diameter and the thickness of the lens body.

The method of making an intraocular lens having a lens body and at least a pair of position fixation elements 11, 12 connected with the lens body 10, a second portion 12b of a position fixation element being pivotable about the end of a first portion 12a thereof, comprises measuring predetermined dimensions of the eye, for example, the upper and lower regions 18 and 19 respectively of the groove behind scleral spur 20 represented in FIG. 7.

The method also includes pivoting the second portion 12b about the first portion 12a of a position fixation element to correspond with the measured dimensions of the eye as represented in FIG. 7. The method includes attaching, for example, by sutures or titanium clips through the apertures 12c, 12d, the second portion 12b to the first portion 12a of the position fixation element in the selected position. The lens may then be snaked into the incision into position in the eye as represented in FIG. 7 anteriorly of the iris 21.

The precise dimensions of the lens 10 are in and of themselves not critical aspects of the present invention since the physiological make up of the eyes of different human beings may well dictate the choice of lenses of slightly different dimensional characteristics. Merely by way of example, however, the following dimensions might be present in a representative lens according to the present invention. The lens body diameter A may be 4 mm, its thickness T may be 1.15 mm, and the overall lens length B may be 9 mm, with the distance C from the center of the lens body to the end of each position fixation element 11, 12 being 4.5 mm, respectively, and their thickness t may be 0.2 mm.

Although by virtue of the foregoing arrangement the two position fixation elements 11 and 12 are not coplanar with the lens body, the degree of inclination of the first portion 11a of the first position fixation element 11 and the degree of inclination of the first portion 12a of the second position fixation element 12 are, respectively, such as to dispose the second portion 11b of the first position fixation element and the second portion 12b of the second position fixation element in coplanar relation with each other and with their posterior surfaces at a perpendicular distance J of about 0.25 to 0.75 mm from the posterior surface 10b of the lens body 10a. By virtue of this arrangement, therefore, when the lens 10 has been implanted in the human eye as shown in FIG. 7, the lens body 10a and the proximate portion 11a and section 12b of the two position fixation elements will be maintained out of contact with the iris in the region of the pupil 22, thereby to minimize the possibility of the lens irritating the iris and interfering with the expansion and contraction of the pupil.

While there has been described what is at present considered to be the preferred embodiment of this invention, it will be obvious to those skilled in the art that various changes and modifications may be made therein without departing from the invention, and it is, therefore, aimed to cover all such changes and modifications as fall within the true spirit and scope of the invention.

I claim:

1. An intraocular lens suitable for use as an artificial lens implant anteriorly of the iris, the lens comprising:
a medial, light-focusing lens body; and
at least a pair of lateral position fixation elements connected with said lens body;
at least one of said pair of position fixation elements having a first portion contiguous to and extending generally laterally outwardly from a first region of the periphery of said lens body, and
the other of said pair of position fixation elements having a first portion contiguous to and extending generally laterally outwardly from a second region of the periphery of said lens body spaced from and generally opposite said first region and in a direction generally opposite to that of said first portion of said one position fixation element;
said other of said pair of position fixation elements having a second portion pivotable about the end of said first portion of said other of said pair of position fixation elements before being attached to said first portion of said other of said pair of position fixation elements at a selected position before implantation in the eye.

2. An intraocular lens as claimed in claim 1, wherein said first and second portions of said other of said pair of position fixation elements have overlapping portions with apertures therein, and means extending through selected apertures for attaching said first and second portions of said other of said position fixation elements at a selected relative angular position.

3. An intraocular lens as claimed in claim 1, wherein said one of said pair of position fixation elements has a second portion extending from said first portion generally transversely thereto and at least partly peripherally of said lens body and spaced generally laterally outwardly from a third region of the periphery of said lens body.

4. An intraocular lens as claimed in claim 1, wherein said other position fixation element is provided with means to permit manipulation of the lens comprising a medial aperture in said other position fixation element.

5. An intraocular lens as claimed in claim 3, wherein said position fixation elements are constructed and arranged such that said second portion of said one position fixation element and the tip end region of said other position fixation element coact to provide a three point support for properly positioning the lens in the eye.

6. An intraocular lens as claimed in claim 5, wherein said second portion of said one position fixation element has a middle region of that part of its peripheral edge which faces away from said lens body disposed closer to said lens body than the opposite end regions of that edge, the ends of said second portion of said one position fixation element and said tip end region of said other position fixation element providing said three point support.

7. An intraocular lens in accordance with claim 1 in which said second portion of said other of said pair of position fixation elements is pivotable about the end of said first portion of said other of said pair of position fixation elements before being attached to the end of said first portion of said other of said pair of position fixation elements before implantation in the eye.

8. An intraocular lens in accordance with claim 7 in which, after said second portion of said other of said pair of position fixation elements is attached to the end of said first portion of said other of said pair of position fixation elements, the configurations of said position fixation elements and their location with respect to said lens body are such that the minimum length of a projection of the entire lens onto a plane parallel to the optical axis of said lens body in a direction perpendicular to a projection of said optical axis on said plane which can be achieved by rotating the lens 360° about said optical axis is greater than the minimum length of a projection of said lens body onto said plane in a direction perpendicular to a projection of said optical axis on said plane which can be achieved by rotating said lens body 360° about said optical axis, to an extent sufficient that insertion of the lens into an incision in the eye, by a movement which is generally radial with respect to said optical axis would require the length of such incision to be greater than the minimum possible length of the incision which, as a function of the thickness and lateral dimensions of said lens body, would accommodate and permit passage therethrough of said lens body alone, and the maximum width of each of said position fixation elements at any part thereof for a given thickness thereof is such that each element can be accommodated in and pass longitudinally through said minimum length incision in the eye, whereby the entire lens is capable of being snaked into the eye of the lens implant patient through said minimum length incision.

9. An intraocular lens in accordance with claim 3 wherein the length of said second portion of said one position fixation element is such that it extends along said periphery of said lens body through an arc of between about 40° and about 60°.

10. An intraocular lens as claimed in claim 9 wherein the length of said second portion of said one position fixation element is such that it extends along said periphery of said lens body through an arc of about 45°.

11. An intraocular lens in accordance with claim 1 in which said second portion of said other of said pair of position fixation elements is swivelable about the end of said first portion of said other of said pair of position fixation elements before implantation in the eye.

12. An intraocular lens in accordance with claim 1 in which an end said second portion of said other of said pair of position fixation elements has a concave surface and in which said end of said first portion of said other of said pair of position fixation elements has a convex surface mating with said concave surface.

13. An intraocular lens in accordance with claim 1 in which the position of said second portion of said other of said pair of position fixation elements is adjusted about the end of said first portion of said other of said pair of position fixation elements before implantation in the eye to correspond with measured dimensions of the eye.

14. The method of making an intraocular lens having a lens body and at least a pair of position fixation elements connected with said lens body, a second portion of a position fixation element being pivotable about the end of a first portion thereof, comprising:

measuring predetermined dimensions of the eye;

pivoting said second portion about said first portion of a position fixation element to correspond with the measured dimensions of the eye; and attaching said second portion to said first portion of the position fixation element in the selected position.

* * * * *